US009784922B2

(12) United States Patent
Govari et al.

(10) Patent No.: US 9,784,922 B2
(45) Date of Patent: Oct. 10, 2017

(54) ELECTRO-OPTICAL CONNECTOR WITH HOT ELECTRICAL CONTACT PROTECTION

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 18 days.

(21) Appl. No.: 14/334,792

(22) Filed: Jul. 18, 2014

(65) Prior Publication Data

US 2016/0018602 A1    Jan. 21, 2016

(51) Int. Cl.
*G02B 6/38* (2006.01)
*H01R 9/03* (2006.01)
(Continued)

(52) U.S. Cl.
CPC ......... *G02B 6/3817* (2013.01); *G02B 6/3826* (2013.01); *H01R 9/03* (2013.01); *H01R 13/516* (2013.01); *H01R 24/00* (2013.01); *A61B 5/6846* (2013.01); *A61B 18/1492* (2013.01); *A61B 2018/00178* (2013.01); *G02B 6/3833* (2013.01); *G02B 6/3878* (2013.01); *H01R 2107/00* (2013.01)

(58) Field of Classification Search
CPC .. G02B 6/3817; G02B 6/3826; G02B 6/3833; G02B 6/383; G02B 6/3831; H01R 24/00; H01R 2107/00
USPC ............... 385/53, 59, 92, 100–101, 115, 117
See application file for complete search history.

(56) References Cited

U.S. PATENT DOCUMENTS 3,792,284 A * 2/1974 Kaelin ................. G02B 6/4295
   250/227.24
4,449,784 A * 5/1984 Basov .................. G02B 6/3817
   385/136

(Continued)

FOREIGN PATENT DOCUMENTS

WO    WO 2014/003063 A1    1/2014

OTHER PUBLICATIONS

EP15177227.4—European Extended Search Report—(datedNov. 18, 2015).

*Primary Examiner* — Thomas A Hollweg
*Assistant Examiner* — Guy Anderson
(74) *Attorney, Agent, or Firm* — Louis J. Capezzuto

(57) ABSTRACT

A cable connector, including a housing having a base and a lip, which surrounds the base and defines an aperture configured to receive a mating plug. The cable connector also includes a plurality of electrical contacts enclosed by the housing and configured to convey electrical signals, the electrical contacts having respective first proximal and first distal ends, the first proximal ends being implanted in the base so that the first distal ends are recessed within the aperture at a first distance from the base. The cable connector additionally includes one or more optical fiber terminals containing end portions of respective optical fibers configured to convey optical signals and having respective second proximal and second distal ends, the second proximal ends being implanted in the base so that the second distal ends are recessed within the aperture at a second distance from the base, which is greater than the first distance.

18 Claims, 3 Drawing Sheets

(51) Int. Cl.
*H01R 13/516* (2006.01)
*H01R 24/00* (2011.01)
*A61B 5/00* (2006.01)
*A61B 18/14* (2006.01)
*H01R 107/00* (2006.01)
*A61B 18/00* (2006.01)

(56) References Cited

U.S. PATENT DOCUMENTS

| | | | | |
|---|---|---|---|---|
| 4,595,839 A | * | 6/1986 | Braun | G02B 6/4202 250/227.24 |
| 4,820,185 A | * | 4/1989 | Moulin | H01R 13/621 385/59 |
| 5,108,369 A | * | 4/1992 | Ganguly | A61B 5/0215 604/102.02 |
| 5,108,399 A | * | 4/1992 | Eitenmuller | A61B 17/8047 606/298 |
| 5,109,452 A | * | 4/1992 | Selvin | G02B 6/3817 385/56 |
| 5,242,315 A | * | 9/1993 | O'Dea | G02B 6/3817 385/59 |
| 5,371,819 A | * | 12/1994 | Szegda | G02B 6/3887 385/101 |
| 5,391,199 A | | 2/1995 | Ben-Haim | |
| 5,443,489 A | | 8/1995 | Ben-Haim | |
| 5,518,411 A | | 5/1996 | Belleci | |
| 5,521,996 A | | 5/1996 | Ames | |
| 5,558,091 A | | 9/1996 | Acker | |
| 5,722,842 A | * | 3/1998 | Cairns | G02B 6/3816 439/139 |
| 5,868,664 A | * | 2/1999 | Speier | A61B 1/042 348/73 |
| 5,944,022 A | | 8/1999 | Nardella | |
| 5,983,126 A | | 11/1999 | Wittkampf | |
| 6,004,044 A | * | 12/1999 | Paulus | G02B 6/4249 385/88 |
| 6,164,838 A | | 12/2000 | Maehara | |
| 6,167,291 A | | 12/2000 | Barajas | |
| 6,172,499 B1 | | 1/2001 | Ashe | |
| 6,177,792 B1 | | 1/2001 | Govari | |
| 6,456,864 B1 | | 9/2002 | Swanson | |
| 6,494,739 B1 | * | 12/2002 | Vivenzio | H01R 13/5804 358/473 |
| 6,690,963 B2 | | 2/2004 | Ben-Haim | |
| 6,733,186 B2 | * | 5/2004 | Pfleger | G02B 6/4293 385/128 |
| 6,788,967 B2 | | 9/2004 | Ben-Haim | |
| 6,814,625 B2 | * | 11/2004 | Richmond | H01R 13/6453 439/157 |
| 6,827,597 B1 | | 12/2004 | Metzbower et al. | |
| 6,913,402 B2 | * | 7/2005 | Bohlin | G02B 6/4292 385/53 |
| 7,350,981 B2 | * | 4/2008 | Durrant | G02B 6/3825 385/55 |
| 7,481,584 B2 | * | 1/2009 | Cairns | H01R 13/5219 385/60 |
| 7,556,528 B1 | * | 7/2009 | Ju | H01R 24/60 439/541.5 |
| 7,674,046 B2 | * | 3/2010 | Milette | G02B 6/3831 385/53 |
| 8,974,126 B2 | * | 3/2015 | Sloey | G02B 6/3817 385/93 |
| 2003/0156798 A1 | * | 8/2003 | Cull | G02B 6/3817 385/71 |
| 2004/0157499 A1 | * | 8/2004 | Nania | H01R 13/6599 439/680 |
| 2004/0161203 A1 | * | 8/2004 | Cull | G02B 6/3817 385/71 |
| 2005/0203404 A1 | * | 9/2005 | Freiburger | A61B 8/06 600/453 |
| 2006/0056769 A1 | | 3/2006 | Khemakhem et al. | |
| 2008/0003868 A1 | * | 1/2008 | Cairns | H01R 13/5219 439/552 |
| 2008/0281157 A1 | * | 11/2008 | Miyagi | A61B 1/00126 600/132 |
| 2009/0093806 A1 | | 4/2009 | Govari | |
| 2009/0138007 A1 | | 5/2009 | Govari | |
| 2010/0158448 A1 | * | 6/2010 | Yi | G02B 6/3817 385/74 |
| 2012/0148196 A1 | | 6/2012 | Penumatcha | |
| 2012/0301084 A1 | * | 11/2012 | Kozischek | G02B 6/3897 385/76 |
| 2013/0035550 A1 | * | 2/2013 | Watanabe | A61B 1/00121 600/132 |
| 2013/0078842 A1 | * | 3/2013 | Lee | H01R 13/6275 439/352 |
| 2013/0087690 A1 | * | 4/2013 | Sloey | G02B 6/3817 250/216 |
| 2013/0089290 A1 | * | 4/2013 | Sloey | G02B 6/3817 385/74 |
| 2013/0249292 A1 | | 9/2013 | Blackwell, Jr. | |
| 2014/0002101 A1 | * | 1/2014 | Lussier | G01R 31/04 324/537 |
| 2014/0064679 A1 | * | 3/2014 | Register, III | G02B 6/4416 385/101 |
| 2015/0110444 A1 | | 4/2015 | Tanaka et al. | |

* cited by examiner

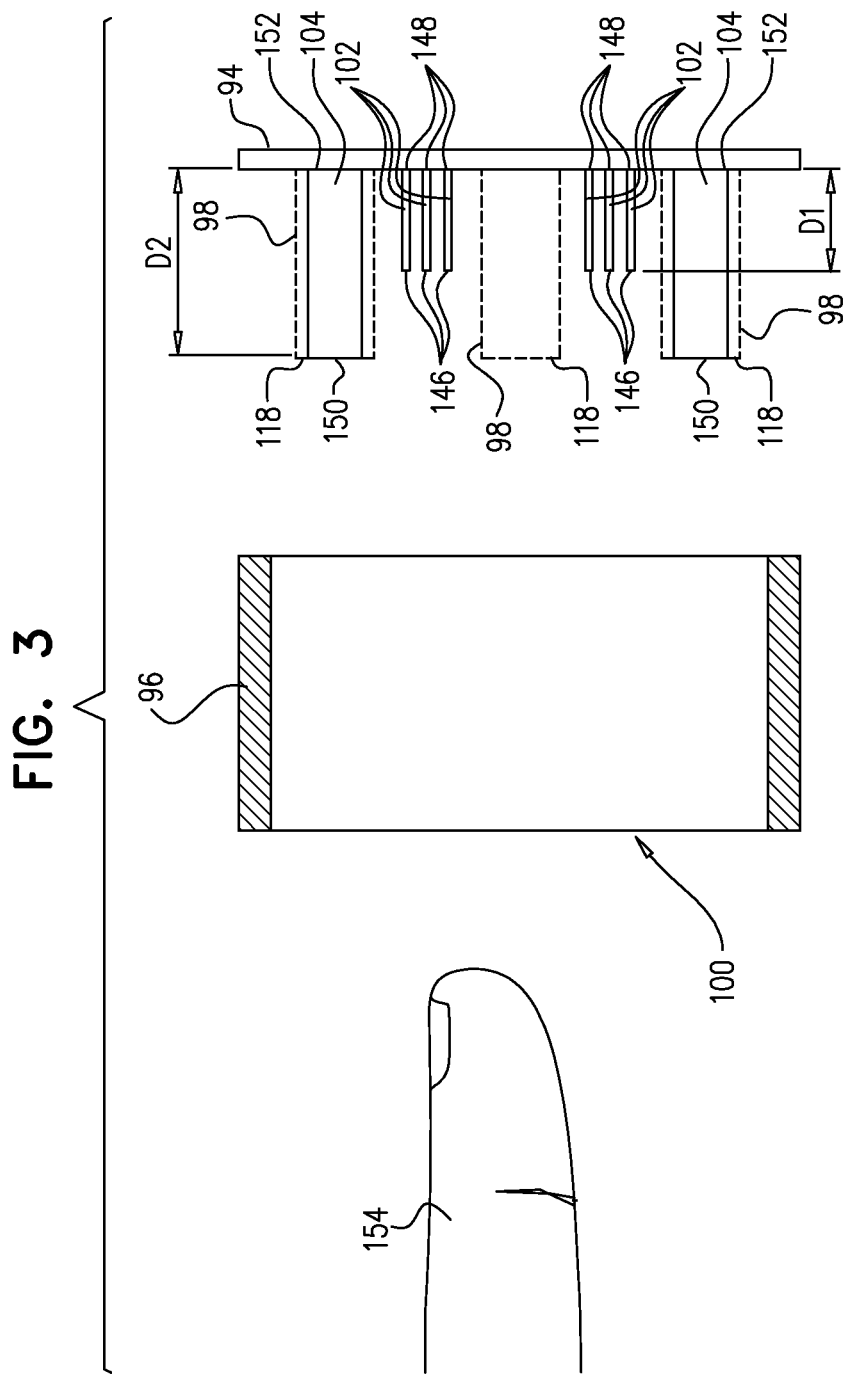

ELECTRO-OPTICAL CONNECTOR WITH HOT ELECTRICAL CONTACT PROTECTION

FIELD OF THE INVENTION

The present invention relates generally to connectors, and specifically to connectors intended for use in a medical procedure.

BACKGROUND OF THE INVENTION

A catheter may comprise a relatively large number of wires and optical fibers within the catheter tube, for the purpose of conveying signals between distal and proximal ends of the catheter. Coupling proximal ends of the wires and the optical fibers to a console may require a connector that is demanding in its specification, in order to meet all the requirements of medical equipment that is used in an invasive procedure.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention a cable connector, including a housing having a base and a lip, which surrounds the base and defines an aperture configured to receive a mating plug, a plurality of electrical contacts enclosed by the housing and configured to convey electrical signals, the electrical contacts having respective first proximal and first distal ends, the first proximal ends being implanted in the base so that the first distal ends are recessed within the aperture at a first distance from the base, and one or more optical fiber terminals containing end portions of respective optical fibers configured to convey optical signals and having respective second proximal and second distal ends, the second proximal ends being implanted in the base so that the second distal ends are recessed within the aperture at a second distance from the base, which is greater than the first distance.

In some embodiments, the electrical signals are selected from a list consisting of radio frequency (RF) energy and sensor measurements. In additional embodiments, the optical signals are selected from a list consisting of optical radiation and data. In further embodiments, the housing and the one or more optical fiber terminals may include a non-conductive material. In supplemental embodiments, the one or more optical fiber terminals may include a conductive material which is grounded. In additional embodiments, the cable connector may include one or more structures protruding from the base, wherein each of the one or more optical fiber terminals is contained within a corresponding structure.

In some embodiments, the one or more optical fiber terminals may include one or more male optical fiber terminals, wherein the plurality of electrical contacts may include female contact sockets. In further embodiments, the cable connector may include a mating plug configured for insertion into the housing, the mating plug including a corresponding male contact pin for each of the plurality of female contact sockets, and a corresponding female optical fiber terminal for each of the one or more male optical fiber terminals. In supplemental embodiments, a combination of a given male optical fiber terminal and the corresponding female plug optical fiber terminal may include an optical fiber connector selected from a list consisting of a ferrule connector, a biconical connector, an expanded beam connector and a multi-fiber connector.

There is also provided, in accordance with an embodiment of the present invention a method, including providing a housing having a base and a lip, which surrounds the base and defines an aperture configured to receive a mating plug, enclosing a plurality of electrical contacts within the housing, configuring the plurality of electrical contacts to convey electrical signals, the electrical contacts having respective first proximal and first distal ends, implanting the first proximal ends in the base so that the first distal ends are recessed within the aperture at a first distance from the base, enclosing, within the housing, one or more optical fiber terminals containing end portions of respective optical fibers, configuring the one or more optical fiber terminals to convey optical signals, the one or more optical fiber terminals having respective second proximal and second distal ends, and implanting the second proximal ends in the base so that the second distal ends are recessed within the aperture at a second distance from the base, which is greater than the first distance.

BRIEF DESCRIPTION OF THE DRAWINGS

The disclosure is herein described, by way of example only, with reference to the accompanying drawings, wherein:

FIG. 3 is a schematic cross-sectional view of the electro-optical connector, in accordance with an embodiment of the present invention.

DETAILED DESCRIPTION OF EMBODIMENTS

Overview

Embodiments of the present invention provide an electro-optical connector (also referred to herein as a connector) configured to prevent a finger from touching any of a plurality of electrical contacts that are "hot" (i.e., electrical contacts conveying electrical signals such as radio frequency energy). In addition to the electrical contacts, the connector comprises one or more optical fiber terminals, a base, and a lip which surrounds the base and defines an aperture configured to receive a mating plug.

In some embodiments, the electrical contacts are enclosed by a housing, and have respective first proximal and first distal ends. As explained hereinbelow, the first proximal ends are implanted in the base so that the first distal ends are recessed within the aperture at a first distance from the base.

The one or more optical fiber terminals may contain end portions of respective optical fibers configured to convey optical signals, and have respective second proximal and second distal ends. In some embodiments, the second proximal ends are implanted in the base so that the second distal ends are recessed within the aperture at a second distance from the base, which is greater than the first distance.

Since the second distal ends of the one or more optical fiber terminals are closer to the lip than first distal ends of the electrical contacts, connectors implementing embodiments of the present invention can help prevent an operator's finger entering the aperture from touching the electrical contacts, thereby protecting the operator, the patient, and any equipment coupled to the connector.

System Description

Figure 1:
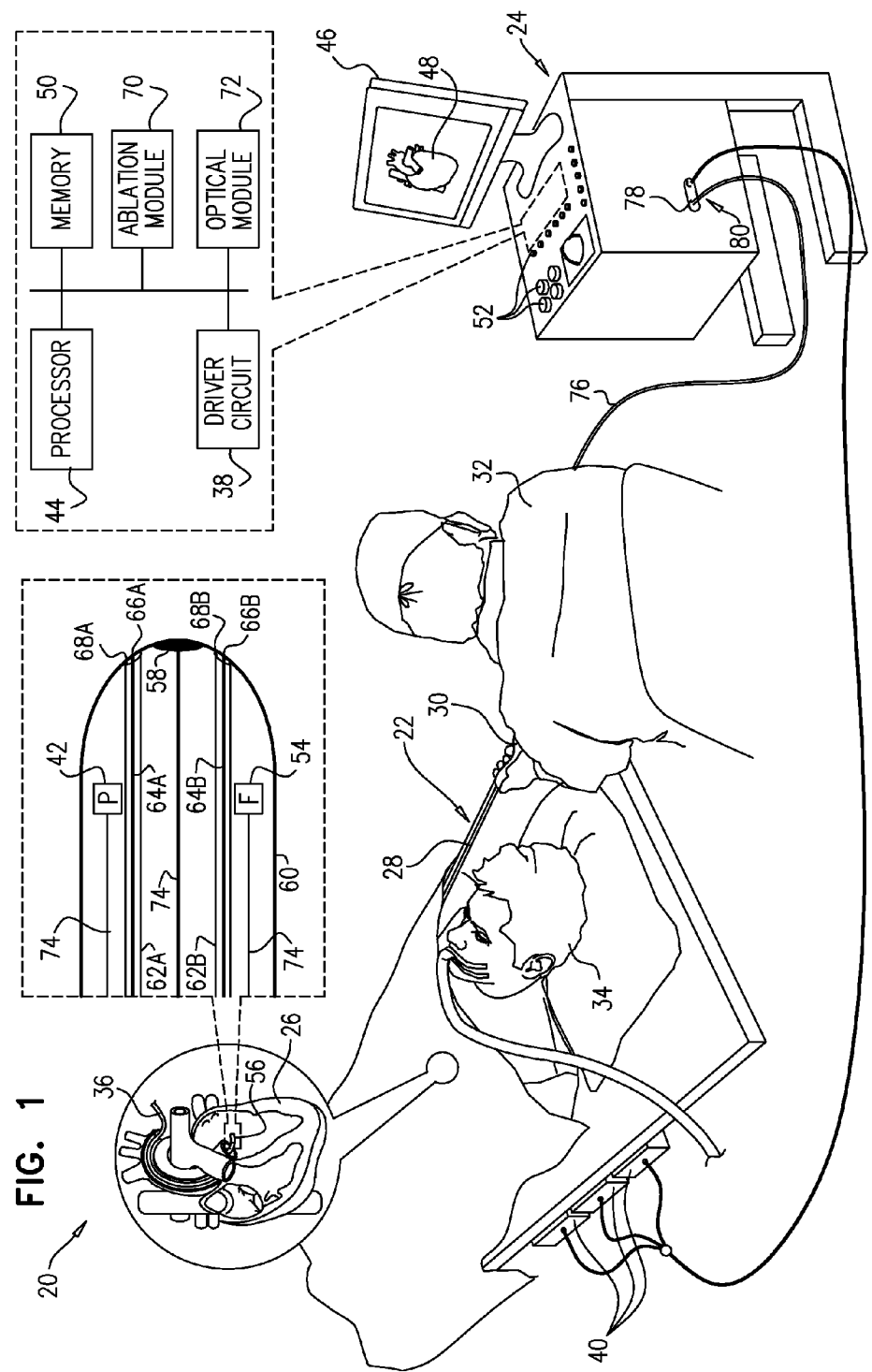
FIG. 1 is a schematic pictorial illustration of a medical system comprising an electro-optical connector with hot electrical contact protection, in accordance with an embodiment of the present invention.

FIG. 1 is a schematic pictorial illustration of a medical system 20, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as performing ablation of heart tissue in a heart 26. Alternatively, probe 22 may be used, mutatis mutandis, for other therapeutic and/or diagnostic purposes in the heart or in other body organs.

Probe 22 comprises a flexible insertion tube 28, and a handle 30 coupled to a proximal end of the insertion tube. By manipulating handle 30, an operator 32 can insert probe 22 into a body cavity in a patient 34. For example, operator 32 can insert probe 22 through the vascular system of a patient 34 so that a distal end 36 of probe 22 enters a chamber of heart 26 and engages endocardial tissue at a desired location or locations.

System 20 typically uses magnetic position sensing to determine position coordinates of distal end 36 inside heart 26. Console 24 comprises a driver circuit 38 which drives field generators 40 to generate magnetic fields within the body of patient 34. Typically, field generators 40 comprise coils, which are placed below the patient's torso at known positions external to patient 34. These coils generate magnetic fields in a predefined working volume that contains heart 26. A magnetic field sensor 42 (also referred to herein as position sensor 42) within distal end 36 of probe 22 generates electrical signals in response to the magnetic fields from the coils, thereby enabling console 24 to determine the position of distal end 36 within the chamber.

Although in the present example system 20 measures the position of distal end 36 using magnetic-based sensors, other position tracking techniques may be used (e.g., impedance-based sensors). Magnetic position tracking techniques are described, for example, in U.S. Pat. Nos. 5,391,199 and 6,690,963 referenced above, and in U.S. Pat. Nos. 5,443,489, 6,788,967, 5,558,091, 6,172,499 and 6,177,792, whose disclosures are incorporated herein by reference. Impedance-based position tracking techniques, are described, for example, in U.S. Pat. Nos. 5,983,126, 6,456,864 and 5,944,022, whose disclosures are incorporated herein by reference. Both systems generate signals which vary according to the position of distal end 36.

A processor 44 processes these signals in order to determine the position coordinates of distal end 36, typically including both location and orientation coordinates. The method of position sensing described hereinabove is implemented in the above-mentioned CARTO™ system and is described in detail in the patents and patent applications cited herein.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

Based on the signals received from probe 22 and other components of system 20, processor 44 drives a display 46 to present operator 32 with an image 48 showing the position of distal end 36 in the patient's body, as well as status information and guidance regarding the procedure that is in progress. Processor 44 stores data representing image 48 in a memory 50. In some embodiments, operator 32 can manipulate image 48 using one or more input devices 52.

Probe 22 typically also comprises a force sensor 54 contained within distal end 36. Force sensor 54 measures a force applied by a distal tip 56 of probe 22 to endocardial tissue of heart 26 by generating a signal to the console that is indicative of the force exerted by the distal tip on the endocardial tissue. In one embodiment, the force sensor may comprise a magnetic field transmitter and receiver connected by a spring in distal tip 56, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 36 may comprise another type of force sensor.

In the present embodiment, an electrode 58 is mounted on distal end 36. Electrode 58 typically comprises a thin metal layer formed over an insulating sheath 60 of insertion tube 28. Probe 22 comprises channels 62 within insertion tube 28 and distal end 36 that are configured to hold optical fibers 64 having respective distal tips 66. Transparent windows 68 are mounted on distal end 36, and are configured to enable optical radiation (i.e., light) to pass through the windows.

In the example shown in FIG. 1, channels 62, optical fibers 64, distal tips 66 and windows 68 may be differentiated by appending a letter to the identifying numeral so that the channels comprise channels 62A and 62B, the optical fibers comprise optical fibers 64A and 64B, the distal tips of the optical fibers comprise distal tips 66A and 66B, and windows 68 comprise windows 68A and 68B. In some embodiments, optical fiber 64A can be configured to transmit, via distal tip 66A and window 68A, optical radiation in order to irradiate endocardial tissue in proximity to distal tip 56, and optical fiber 64B can be configured to acquire, via window 68B and distal tip 66B, optical radiation returning from the irradiated tissue.

Console 24 also comprises a radio frequency (RF) ablation module 70 and an optical module 72. Processor 44 uses the ablation module to monitor and control ablation parameters such as the level of ablation power applied via electrode 58. The ablation module may also monitor and control the duration of the ablation that is provided. Ablation module 70 conveys ablation power to electrode 58 via a first electrical line 74. In the configuration shown in FIG. 1, position sensor 42 and force sensor 54 convey respective measurements to processor 44 via additional electrical lines 74.

Optical module 72 is configured to manage optical signals carried by optical fibers 64. In the example described hereinabove, optical module 72 conveys optical radiation to optical fiber 64A (i.e., for transmission through window 68A), and processes optical radiation conveyed by optical fiber 64B that was received through window 68B. In alternative configurations, optical module 72 can be configured to manage other types of data carried by optical fibers 64. For example, the optical fibers may convey location measurements from position sensor 42 and force measurements from force sensor 54 (or measurements from any other type of sensor).

A cable 76 coupled to handle 30 and console 24 comprises electrical lines 74 and optical fibers 64. As described in FIGS. 2 and 3 hereinbelow, a cable connector 78 (also referred to herein as an electro-optical connector) couples a distal end 80 of cable 76 to console 24.

Figure 2:
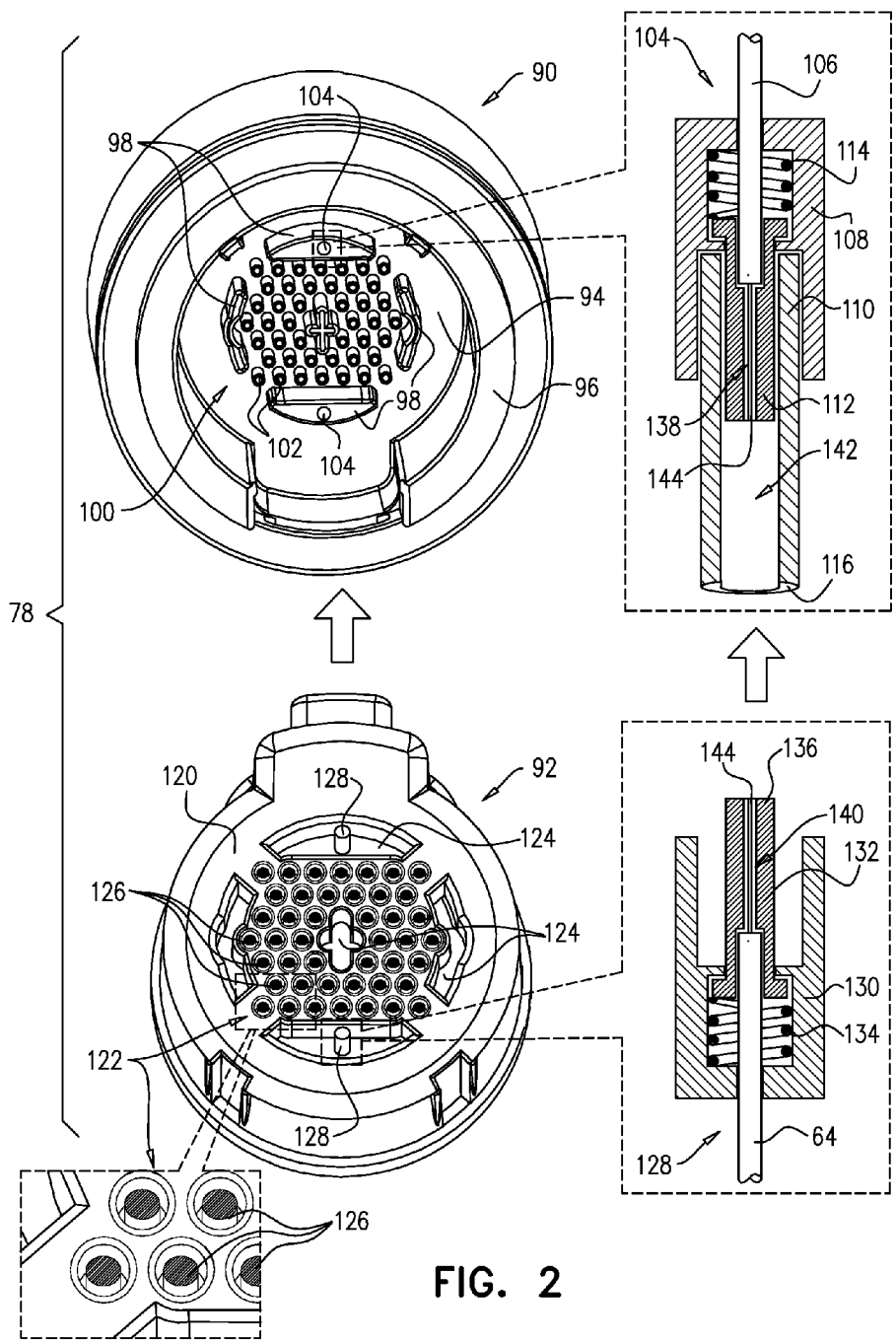
FIG. 2 is a schematic detailed view of the electro-optical connector, in accordance with an embodiment of the present invention.

FIGS. 2 and 3 are schematic detailed views of cable connector 78, in accordance with an embodiment of the present invention. Cable connector 78 comprises a housing 90 mounted on console 24, and a mating plug 92 coupled to distal end 80. Housing 90 may be formed of a polymer, for example a polycarbonate, and typically by injection molding. Housing 90 comprises a base 94, a lip 96, and structures 98 that protrude from base 94. Lip 96 surrounds base 94, thereby defining an aperture 100 configured to receive mating plug 92. Cable connector 78 also comprises female contact sockets 102 implanted in base 94 and optical fiber terminals 104. In embodiments herein, female contact sockets 102 may also be referred to as electrical contacts 102, and optical fiber terminals 104 may also be referred to as male optical fiber terminals 104.

In the configuration shown in FIGS. 2 and 3, each optical fiber terminal 104 is contained within a given structure 98 (i.e., each optical fiber terminal 104 has a corresponding structure 98). In alternative embodiments, optical fiber terminals 104 are implanted in base 94.

Each optical fiber terminal 104 contains a first end portion of an optical fiber 106 (or first end portions of multiple optical fibers 106) whose second end portion is coupled to optical module 72. Optical fiber terminals 104 comprise an outer sleeve 108, an alignment sleeve 110, a ferrule 112, and an axial spring 114. Outer sleeve 108, alignment sleeve 110 and ferrule 112 are typically tubular structures configured so that outer sleeve 108 encompasses alignment sleeve 110, and alignment sleeve 110 encompasses ferrule 112. In some embodiments, a given optical fiber terminal 104 can be mounted within a given structure 98 so that a distal end 116 of alignment sleeve 110 is flush with a distal end 118 of the given structure, as shown in FIG. 3.

Housing 90 (i.e., base 94, lip 96 and structures 98) is typically are molded using a non-conductive material. In some embodiments optical fiber terminals 104 can also be fabricated using a non-conductive material. In alternative embodiments, optical fiber terminals 104 can be fabricated from a conductive material which is grounded.

Mating plug 92 comprises a base 120 having cavities 122 and 124, and configured for insertion into housing 90. Like housing 90, mating plug 92 may be formed of a polymer, for example a polycarbonate, and typically by injection molding. Mating plug 92 also comprises male contact pins 126 mounted within cavities 122 and optical fiber terminals 128 mounted in cavities 124. In embodiments herein, each optical fiber terminal 128 may also be referred to as a female optical fiber terminal 128.

Each male pin 126 has a corresponding female socket 102, and each female optical fiber terminal 128 has a corresponding male optical fiber terminal 104. As described supra, each optical fiber terminal 104 may be encased within a given structure 98. Therefore, in the configuration shown in FIG. 2, each cavity 124 has a corresponding structure 98.

When mating plug 92 is inserted into housing 90, the insertion mates male contact pins 126 with female sockets 102 and male optical fiber terminals 104 with female optical fiber terminals 128 (i.e., by mating protruding structures 98 with cavities 124). Contact pins 126 and female sockets 102 comprise electrically conductive material, so that mating a given male contact pin 126 with a given socket 102 establishes an electrical connection between console 24 and probe 22.

For example, a first male contact pin 126 can be connected to a proximal end of a first electrical line 74 whose distal end is connected to electrode 58, a second male contact pin 126 can be connected to a proximal end of a second electrical line 74 whose distal end is connected to position sensor 42, and a third male contact pin 126 can be connected to a proximal end of a third electrical line 74 whose distal end is connected to force sensor 54.

The electrical connection between console 24 and probe 22 enables electrical signals to be conveyed between contact pins 126 and sockets 102. Examples of electrical energy include, but are not limited to, radio frequency energy from ablation module 70 and measurements from sensors 42 and 54.

Mating optical fiber terminals 104 and 128 enables a given optical fiber terminal 104 to convey optical signals to a given optical fiber terminal 128 and to convey optical signals from the given optical fiber terminal 128. Examples of optical signals include optical radiation and data. In the configuration shown in FIG. 2, optical fiber terminals 104 and 128 can convey optical radiation from optical module 72, and convey optical radiation from optical fiber 64B. In some embodiments, optical fiber terminals 104 and 128 can be configured to convey analog and/or digital data between console 24 and probe 22.

Each optical fiber terminal 128 contains a first end portion of optical fiber 64 (or first end portions of multiple optical fibers 64) whose second end is inserted in channel 62. Optical fiber terminal 128 comprises an outer sleeve 130, a ferrule 132, and an axial spring 134. Outer sleeve 130 and ferrule 132 are typically tubular structures configured so that outer sleeve 132 encompasses ferrule 132. In some embodiments, a given optical fiber terminal 128 can be mounted within a given cavity 124 so that a proximal end 136 of ferrule 132 protrudes within the given cavity.

Ferrule 112 encompasses a channel 138 configured to convey optical radiation to and/or from optical fiber 106, and ferrule 132 encompasses a channel 142 configured to convey the optical radiation to and/or from optical fiber 64. When mating plug 92 is inserted into housing 90, ferrule 132 enters a first mating cavity 142 in alignment sleeve 110, and the alignment sleeve enters a second mating cavity between outer sleeve 130 and ferrule 132. Upon mating, channels 138 and 140 are aligned so that optical radiation 144 can be conveyed between optical fibers 64 and 106 via the channels.

Each optical fiber terminal 104 and its corresponding optical fiber terminal 128 form an optical fiber connector. While the optical fiber connector shown in FIG. 2 comprises a ferrule connector, other types of optical fiber connectors that can mate optical fibers 64 and 106 are considered to be within the spirit and scope of the present invention. Examples of other types of optical fiber connectors include, but are not limited to, biconical connectors, expanded beam connectors, and multi-fiber connectors.

While the optical fiber connectors shown in FIG. 2 comprise male optical fiber terminals 104 and female optical fiber terminals 128, any other type of optical fiber terminal pair configured to convey optical radiation 144 between optical fibers 64 and 106 is considered to be within the spirit and scope of the present invention. Likewise, while the configuration in FIG. 2 shows female contact sockets 102 and male pins 26, any other pair of electrical connectors configured to convey electrical signals between console 24 and probe 22 is considered to be within the spirit and scope of the present invention.

As shown in FIG. 3, sockets 102 have distal ends 146 and proximal ends 148 that protrude from base 94 so that distal ends 146 are recessed within aperture 100 at a distance $D_1$ from base 94. Each optical fiber terminal 104 has distal ends 150 and proximal ends 152 that protrude from base 94 so that distal ends 150 are recessed within aperture 100 at a distance $D_2$ from base 94. In embodiments of the present invention, distance $D_2$ is greater than distance $D_1$. Therefore, a finger 154 entering aperture 100 will press against the distal end of one or more optical fiber terminals 104 (or the distal end of one or more structures 98 that contain optical fiber terminals 104), and not touch sockets 102.

In some embodiments (as shown in FIG. 2), each socket 102 comprise a tubular structure having a socket aperture at distal end 146 configured to mate with the corresponding male pin 126. The inside of the tubular structure of socket 102 may be lined with a wire braid, so when a given male pin 126 is inserted into a corresponding socket 102, the male pin engages the wire braid, thereby establishing an electrical connection between the given male pin and the corresponding female socket.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A cable connector, comprising:
a housing comprising a base, a lip that surrounds the base and defines an aperture configured to receive a mating plug, and a plurality of structures arranged in the aperture that protrude from the base;
a plurality of electrical contacts enclosed by the housing and configured to convey electrical signals, the electrical contacts having respective first proximal and first distal ends, the first proximal ends being implanted in the base so that the first distal ends are recessed within the aperture at a first distance from the base; and
one or more optical fiber terminals containing end portion of an optical fiber configured to convey optical signals;
wherein the plurality of structures protrude to a second distance from the base, which is greater than the first distance, the plurality of structures comprising:
a central structure disposed centrally within the plurality of electrical contacts;
a plurality of structures regularly spaced around the central structure and arranged to partially surround the plurality of electrical contacts;
at least one of the plurality of structures regularly spaced around the central structure containing the one or more optical fiber terminal;
wherein the arrangement of the plurality of structures is such that when a finger enters the aperture it will press against at least one of the plurality of structures and thereby be prevented from touching the plurality of electrical contacts.

2. The cable connector according to claim 1, wherein the electrical signals are selected from a list consisting of radio frequency (RF) energy and sensor measurements.

3. The cable connector according to claim 1, wherein the optical signals are selected from a list consisting of optical radiation and data.

4. The cable connector according to claim 1, wherein the housing and the one or more optical fiber terminals comprise a non-conductive material.

5. The cable connector according to claim 1, wherein the one or more optical fiber terminals comprise a conductive material which is grounded.

6. The cable connector according to claim 1, wherein the one or more optical fiber terminals comprise one or more male optical fiber terminals, and wherein the plurality of electrical contacts comprise female contact sockets, and comprising a mating plug configured for insertion into the housing, the mating plug comprising a corresponding male contact pin for each of the plurality of female contact sockets, and a corresponding female optical fiber terminal for each of the one or more male optical fiber terminals.

7. The cable connector according to claim 6, wherein a combination of a given male optical fiber terminal and the corresponding female plug optical fiber terminal comprises an optical fiber connector selected from a list consisting of a ferrule connector, a biconical connector, an expanded beam connector and a multi-fiber connector.

8. A method for forming a connector, comprising:
providing a housing comprising a base and a lip, which surrounds the base and defines an aperture configured to receive a mating plug;
enclosing a plurality of electrical contacts within the housing;
configuring the plurality of electrical contacts to convey electrical signals, the electrical contacts having respective first proximal and first distal ends;
implanting the first proximal ends in the base so that the first distal ends are recessed within the aperture at a first distance from the base;
enclosing, within the housing, one or more optical fiber terminals containing end portions of respective optical fibers;
configuring the one or more optical fiber terminals to convey optical signals, the one or more optical fiber terminals having respective second proximal and second distal ends; and
implanting the second proximal ends in the base so that the second distal ends are recessed within the same aperture at a second distance from the base, which is greater than the first distance;
wherein the step of enclosing within the housing further comprises:
protruding a plurality of structures from the base, the plurality of structures comprising:
a central structure disposed centrally within the plurality of electrical contacts;

a plurality of structures regularly spaced around the central structure and arranged to partially surround the plurality of electrical contacts;

at least one of the plurality of structures regularly spaced around the central structure containing the one or more optical fiber terminals; and wherein the plurality of structures protrude to the second distance from the base and are arranged such that in use when a finger enters the aperture it will press against at least one of the plurality of structures and thereby be prevented from touching the plurality of electrical contacts.

9. The method according to claim 8, wherein the electrical signals are selected from a list consisting of radio frequency (RF) energy and sensor measurements.

10. The method according to claim 8, wherein the optical signals are selected from a list consisting of optical radiation and data.

11. The method according to claim 8, wherein the housing and the one or more optical fiber terminals comprise a non-conductive material.

12. The method according to claim 8, wherein the one or more optical fiber terminals comprise a conductive material which is grounded.

13. The method according to claim 8, wherein the one or more optical fiber terminals comprises one or more male optical fiber terminals, and wherein the plurality of electrical contacts comprise female contact sockets, and comprising configuring a mating plug for insertion into the housing, the mating plug comprising a corresponding male contact pin for each of the plurality of female contact sockets, and a corresponding female optical fiber terminal for each of the one or more male optical fiber terminals.

14. The method according to claim 13, wherein a given male optical fiber terminal and the corresponding female optical fiber terminal comprises an optical fiber connector selected from a list consisting of a ferrule connector, a biconical connector, an expanded beam connector and a multi-fiber connector.

15. The cable connector of claim 1, wherein the cable connector comprises a first and a second optical fiber terminal, wherein each optical fiber terminal is contained in a structure of the plurality of structures regularly spaced around the central structure; and wherein the optical fiber terminal containing structures are arranged to be diametrically opposed to each other relative the central structure.

16. The cable connector of claim 1, wherein the plurality of structures regularly spaced around the central structure comprise two structures each containing one of the first and second optical fiber terminals and two further structures, the structures containing the fiber optical terminals are arranged diametrically opposite to each other relative the central structure and the two further structures are arranged diametrically opposite to each other relative the central structure.

17. The method of claim 8, wherein protruding a plurality of structures from the base further comprises:

protruding a first and a second structure diametrically opposite each other relative to the central structure and arranging the first and second optical fiber terminals such that they are contained in the first and second structures respectively.

18. The method of claim 8, wherein protruding a plurality of structures from the base further comprises:

protruding a first and a second structure diametrically opposite each other relative to the central structure and arranging the first and second optical fiber terminals such that they are contained in the first and second structures respectively; and protruding two further structures diametrically opposite each other relative the central structure.

* * * * *